(12) United States Patent
Nelson et al.

(10) Patent No.: US 10,065,037 B2
(45) Date of Patent: Sep. 4, 2018

(54) SYSTEMS FOR TREATING POST-TRAUMATIC STRESS DISORDER

(71) Applicant: Ohio State Innovation Foundation, Columbus, OH (US)

(72) Inventors: Randy J. Nelson, Dublin, OH (US); Ali R. Rezai, Columbus, OH (US); Zachary M. Weil, Columbus, OH (US)

(*) Notice: Subject to any disclaimer, the term of this patent is extended or adjusted under 35 U.S.C. 154(b) by 0 days.

(21) Appl. No.: 14/850,155

(22) Filed: Sep. 10, 2015

(65) Prior Publication Data

US 2015/0374994 A1 Dec. 31, 2015

Related U.S. Application Data

(63) Continuation-in-part of application No. PCT/US2014/022407, filed on Mar. 10, 2014.

(60) Provisional application No. 61/775,997, filed on Mar. 11, 2013.

(51) Int. Cl.
   *A61N 1/36* (2006.01)
   *A61N 1/05* (2006.01)
   *A61N 2/00* (2006.01)

(52) U.S. Cl.
   CPC ....... *A61N 1/36096* (2013.01); *A61N 1/0551* (2013.01); *A61N 1/3606* (2013.01); *A61N 1/36139* (2013.01); *A61N 2/006* (2013.01)

(58) Field of Classification Search
   CPC .............. A61N 1/36096; A61N 1/0551; A61N 1/3606; A61N 1/36139; A61N 2/006
   USPC ......................................................... 607/46
   See application file for complete search history.

(56) References Cited

U.S. PATENT DOCUMENTS

| 5,716,377 A | 2/1998 | Rise et al. |
| 7,917,206 B2 | 3/2011 | Frei et al. |
| 7,974,696 B1* | 7/2011 | DiLorenzo ........... A61B 5/0476 607/2 |
| 2003/0216792 A1 | 11/2003 | Levin et al. |
| 2007/0038264 A1 | 2/2007 | Jaax et al. |
| 2007/0135871 A1* | 6/2007 | Lipov .................. A61K 9/0019 607/89 |
| 2007/0179557 A1* | 8/2007 | Maschino .............. A61N 2/008 607/45 |

(Continued)

OTHER PUBLICATIONS

International Search Report for corresponding Pat. Appl. No. PCT/US2014/022407, dated May 15, 2014, 4 pages.

*Primary Examiner* — Carl H Layno
*Assistant Examiner* — Erin M Piateski
(74) *Attorney, Agent, or Firm* — FisherBroyles, LLP; James W. Hill

(57) ABSTRACT

One aspect of the present disclosure relates to a closed-loop therapy system for treating post-traumatic stress disorder (PTSD) in a subject. The therapy delivery system can include a sensing component, a delivery component, and a controller. The sensing component can be configured to detect at least one physiological parameter associated with PTSD. The delivery component can be configured for implantation on or about a ganglion of the sympathetic nervous system (SNS). The controller can be configured to automatically coordinate operation of the sensing and delivery components. The controller can also be configured to deliver an electrical signal to the delivery component so that activity of the ganglion of the SNS is substantially blocked without enhancing a symptom of PTSD.

12 Claims, 4 Drawing Sheets

(56) References Cited

U.S. PATENT DOCUMENTS

| | | | |
|---|---|---|---|
| 2010/0191304 A1* | 7/2010 | Scott | A61B 5/0476 607/45 |
| 2010/0204568 A1* | 8/2010 | Narouze | A61B 8/08 600/424 |
| 2011/0224749 A1 | 9/2011 | Ben-David et al. | |
| 2011/0270359 A1 | 11/2011 | Colborn | |

* cited by examiner

SYSTEMS FOR TREATING POST-TRAUMATIC STRESS DISORDER

RELATED APPLICATION

This application is a continuation-in-part application of PCT Application No. PCT/US2014/022407, filed on Mar. 10, 2014, which claims priority to U.S. Provisional Patent Application Ser. No. 61/775,997, filed Mar. 11, 2013, the entirety of all applications is hereby incorporated by reference for all purposes.

TECHNICAL FIELD

The present disclosure relates generally to neuromodulatory devices, systems and methods, and more particularly to devices, systems, and methods for treating post-traumatic stress disorder.

Post-traumatic stress disorder (PTSD) is a pathological anxiety that occurs when an individual experiences or witnesses severe trauma that constitutes a threat to his/her physical integrity or that of another person. The individual initially responds with intense fear, a sense of hopelessness, or horror; later he or she may re-experience the event, with resultant symptoms of numbness, avoidance, hypervigilance and hyperarousal. These symptoms lead to clinically significant distress and/or fractional impairment.

Traditionally, medical approaches to PTSD have relied upon pharmacological agents with heavy utilization of selective serotonin reuptake inhibitors (SSRIs), which affect the levels of serotonin in the brass. The challenge is that although these medications have relatively low rates of significant side-effects, only 50% to 60% of patients enjoy any appreciable reduction in symptoms. Further, SSRIs can take up to eight weeks to achieve a clinical response, and are associated with a high drop-out rate. Other approaches include light therapy and exposure therapy, but the efficacy of each depends upon treatment duration and compliance.

SUMMARY

The present disclosure relates generally to neuromodulatory devices, systems and methods, and more particularly to devices, systems, and methods for treating post-traumatic stress disorder (PTSD).

One aspect of the present disclosure relates to a closed-loop therapy system for treating PTSD in a subject. The therapy delivery system can include a sensing component, a delivery component, and a controller. The sensing component can be configured to detect at least one physiological parameter associated with PTSD. The delivery component can be configured for implantation on or about a ganglion of the sympathetic nervous system (SNS). The controller can be configured to automatically coordinate operation of the sensing and delivery components. The controller can also be configured to deliver as electrical signal to the delivery component so that activity of the ganglion of the SNS is substantially blocked without enhancing a symptom of PTSD.

Another aspect of the present disclosure relates to a method for treating PTSD in a subject. One step of the method can include placing a therapy delivery device into electrical communication with a ganglion of the SNS associated with PTSD. Next, the therapy delivery device can be activated to deliver an electrical signal to the ganglion of the SNS so that activity of the ganglion of the SNS is substantially blocked without enhancing a symptom of PTSD.

Another aspect of the present disclosure relates to a method for treating PTSD in a subject. One step of the method can comprise implanting a therapy delivery device within the subject. Next, the therapy delivery device is placed into electrical communication with the stellate ganglion. The therapy delivery device is then activated to deliver an electrical signal to the stellate ganglion so that activity of the ganglion of the SNS is substantially blocked without enhancing a symptom of PTSD.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
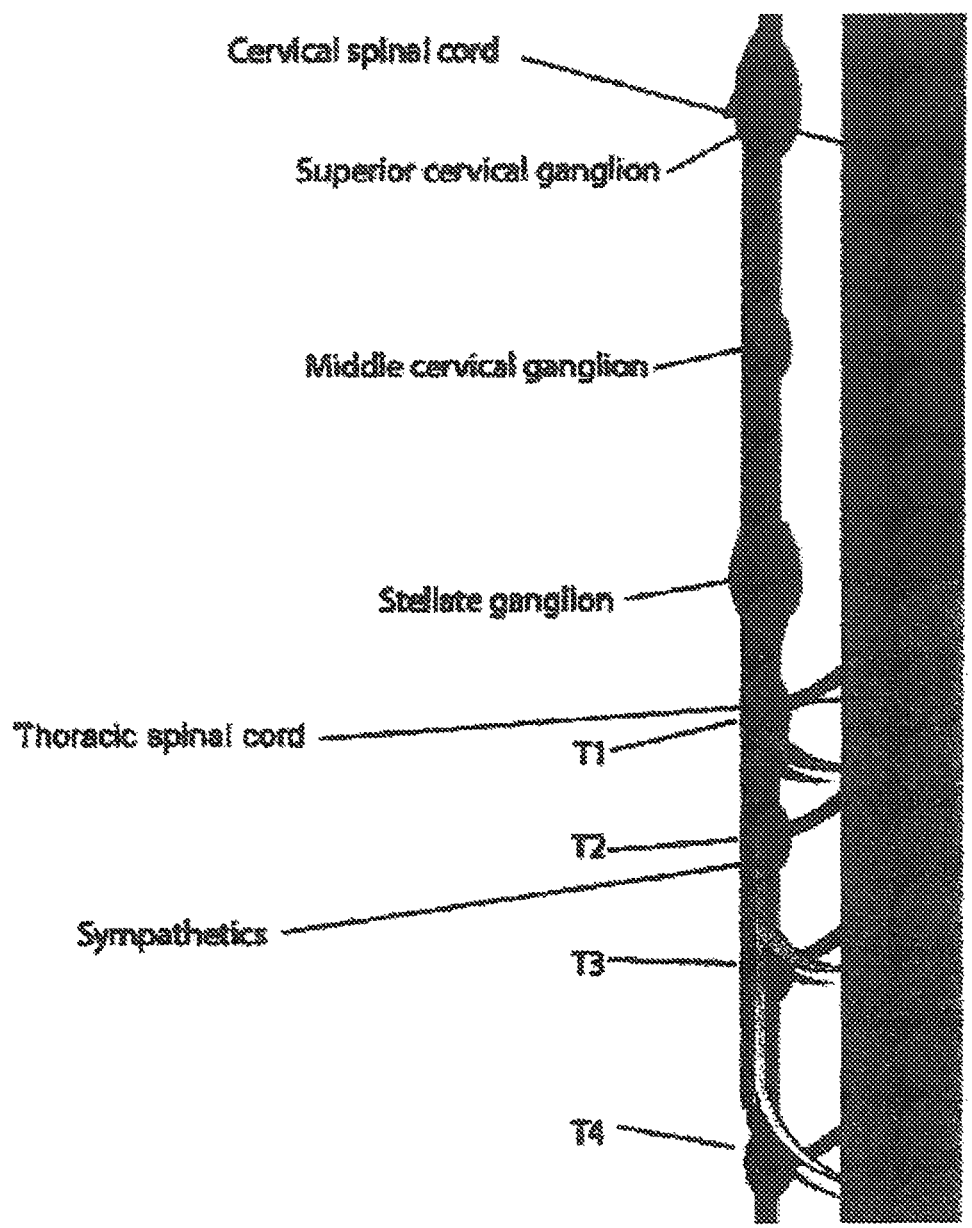
FIG. 1 is schematic illustration showing the cervical and upper thoracic portions of the sympathetic nerve chain and the spinal cord.

Unless defined otherwise, all technical and scientific terms used herein have the same meaning as is commonly understood by one of skill in the art to which the present disclosure pertains.

In the context of the present disclosure, the term "sympathetic nervous tissue" cars refer to any tissues of the sympathetic nervous system (SNS) including, but not limited to, neurons, axons, fibers, tracts, nerves, plexus, afferent plexus fibers, efferent plexus fibers, ganglia, pre-ganglionic fibers, post-ganglionic fibers, cervical ganglia/ganglion, a cervicothoracic or stellate ganglion, thoracic ganglion/ganglion, afferents, efferents, and combinations thereof.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the terms "modulate" or "modulating" with reference so sympathetic nervous tissue can refer to causing a change in neuronal activity, chemistry and/or metabolism. The change can refer to an increase, decrease, or even a change in a patters of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the terms "substantially blocked" or "substantially block" when used with reference to sympathetic nervous tissue activity can refer to a complete (e.g., 100%) or partial inhibition (e.g., less than 100%, such as about 90%, about 80%, about 70%, about 60%, or less than about 50%) of nerve conduction through the sympathetic nervous tissue.

As used herein, the term "activity" when used with reference to sympathetic nervous tissue can, in some instances, refer to the ability of a sympathetic nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on sympathetic nervous tissue.

As used herein, the terms "post-traumatic stress disorder" or "PTSD" can refer to a pathological anxiety that occurs when an individual experiences or witnesses severe trauma that constitutes a threat to his/her physical integrity or that of another person.

As used herein, the terms "treat" or "treating" can refer to therapeutically regulating, preventing, improving, alleviating the symptoms of, and/or reducing the effects of PTSD. As such, treatment also includes situations where PTSD, or at least symptoms associated therewith, is completely inhibited, e.g., prevented from happening or stopped (e.g., terminated) such that the subject no longer suffers from PTSD, or at least the symptoms that characterize PTSD.

As used herein, the phrase "diagnosed with PTSD" can refer to having a diagnosis of at least one sign, symptom, or symptom cluster indicative of PTSD. Non-limiting examples of such traumatic events can include military combat, terrorist incidents, physical assault, sexual assault, motor vehicle accidents, and natural disasters.

The Diagnostic and Statistical Manual of Mental Disorders-IV-Text revised (DSM-IV-TR), a handbook for mental health professionals that lists categories of mental disorders and the criteria, classifies PTSD as an anxiety disorder. According to the DSM-IV-TR, a PTSD diagnosis can be made if:

1. the patient experienced, witnessed, or was confronted with an event or events that involved actual or threatened death or serious injury, or a threat to the physical integrity of self or others and the response involved intense fear, helplessness, or horror;

2. as a consequence of the traumatic event, the patient experiences at least one re-experiencing/intrusion symptom, three avoidance/numbing symptoms, and two hyperarousal symptoms, and the duration of the symptoms is for more than 1 month; and 3. the symptoms cause clinically significant distress or impairment in social, occupational, or other important areas of functioning.

In some instances, if the patient's disorder fulfills DSM-IV-TR criteria, the patient is diagnosed with PTSD. In other instances, if the patient has at least one sign, symptom, or symptom cluster of PTSD, the patient is diagnosed with PTSD. Its further instances, a scale can be used to measure a sign, symptom, or symptom cluster of PTSD, and PTSD can be diagnosed on the basis of the measurement using that scale. In some instances, a "score" on a scale can be used to diagnose or assess a sign, symptom, or symptom cluster of PTSD. In other instances, a "score" can measure at least one of the frequency, intensity, or severity of a sign, symptom, or symptom cluster of PTSD.

As used herein, the term "scale" can refer to a method to measure at least one sign, symptom, or symptom cluster of PTSD to a patient. In some instances, a scale may be an interview or a questionnaire. Non-limiting examples of scales include Clinician-Administered PTSD Scale (CAPS), Clinician-Administered PTSD Scale Part 2 (CAPS-2), Clinician-Administered PTSD Scale for Children and Adolescents (CAPS-CA), Impact of Event Scale (IES), Impact of Event Scale-Revised (IES-R), Clinical Global Impression Scale (CGI), Clinical Global Impression Severity of Illness (CGI-S), Clinical Global Impression Improvement (CGI-I), Duke Global Rating for PTSD scale (DGRP), Duke Global Rating for PTSD scale Improvement (DGRP-I), Hamilton Anxiety Scale (HAM-A), Structured Interview for PTSD (SI-PTSD), PTSD Interview (PTSD-I), PTSD Symptom Scale (PSS-I), Mini International Neuropsychiatric Interview (MINI), Montgomery-Åsberg Depression Rating Scale (MADRS), Beck Depression Inventory (BDI), Hamilton Depression Scale (HAM-D), Revised Hamilton Rating Scale for Depression (RHRSD), Major Depressive Inventory (MDI), Geriatric Depression Scale (GDS-30), and Children's Depression Index (CDI).

As used herein, the terms "sign" and "signs" can refer to objective findings of a disorder (e.g., PTSD). In some instances, a sign can be a physiological manifestation or reaction of a disorder (e.g., PTSD). For example, a sign may include heart rate and rhythm, body temperature, pattern and rate of respiration, papillary changes and blood pressure. In other instances, signs can be associated with, or indicative of, symptoms.

As used herein, the terms "symptom" and "symptoms" can refer to subjective indications that characterize a disorder. Symptoms of PTSD may refer to, for example, recurrent and intrusive trauma recollections, recurrent and distressing dreams of the traumatic event, acting or feeling as if the traumatic event were recurring, distress when exposed to trauma reminders, physiological reactivity when exposed to trauma reminders, efforts to avoid thoughts or feelings associated with the trauma, efforts to avoid activities or situations, inability to recall trauma or trauma aspects, markedly diminished interest in significant activities, feelings of detachment or estrangement from others, restricted range of affect, sense of a foreshortened future, social anxiety, anxiety with unfamiliar surroundings, difficulty falling or staying asleep, irritability or outbursts of anger, difficulty concentrating, hypervigilance, and exaggerated startle response. In some instances, the physiological reactivity manifests in at least one of abnormal respiration, abnormal cardiac rate of rhythm, abnormal blood pressure, abnormal function of a special sense, and abnormal function of sensory organ. In other instances, restricted range of effect characterized by diminished or restricted range or intensity of feelings or display of feelings can occur and a sense of a foreshortened future can manifest in thinking that one will not have a career, marriage, children, or a normal life span. In further instances, children and adolescents may have symptoms of PTSD, such as disorganized or agitated behavior, repetitive play that expresses aspects of the trauma, frightening dreams which lack recognizable content, and trauma-specific reenactment.

As used herein, the term "symptom cluster" can refer to a set of signs, symptoms, or a set of signs and symptoms that are grouped together because of their relationship to each other or their simultaneous occurrence. In some instances, for example, PTSD is characterized by three symptom clusters: re-experiencing/intrusion; avoidance/numbing; and hyperarousal.

As used herein, the term "re-experiencing/intrusion" can refer to at least one of recurrent and intrusive trauma recollections, recurrent and distressing dreams of the traumatic event, acting or feeling as if the traumatic event were recurring, distress when exposed to trauma reminders, and physiological reactivity when exposed to trauma reminders. In some instances, the physiological reactivity can manifest in at least one of abnormal respiration, abnormal cardiac rate of rhythm, abnormal blood pressure, abnormal function of a special sense, and abnormal function of sensory organ.

As used herein, the term "avoidance/numbing" can refer to at least one of efforts to avoid thoughts or feelings associated with the trauma, efforts to avoid activities or situations, inability to recall trauma or trauma aspects, markedly diminished interest is significant activities, feelings of detachment or estrangement from others, restricted range of affect, and sense of a foreshortened future. Restricted range of effect characterized by diminished or restricted range or intensity of feelings or display of feelings can occur. A sense of a foreshortened future can manifest in thinking that one will not have a career, marriage, children, or a normal life span. Avoidance/numbing can also manifest in social anxiety and anxiety with unfamiliar surroundings.

As used herein, the term "hyperarousal" can refer to at least one of difficulty falling or staying asleep, irritability or outbursts of anger, difficulty concentrating, hypervigilance, and exaggerated startle response.

Overview

A brief discussion of the pertinent neurophysiology is provided to assist the reader with understanding certain aspects of the present disclosure. The nervous system is divided into the somatic nervous system and the autonomic nervous system (ANS). In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organism's internal resources to perform physiological functions for the benefit of the organism, e.g., responds to environment conditions in a manner that is advantageous to the organism. The ANS acts through a balance of its two components: the SNS and the parasympathetic nervous system (PNS), which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The SNS is the part of the ANS comprising nerve fibers that leave the spinal cord in the thoracic and lumbar regions and supply viscera and blood vessels by way of a chain of sympathetic ganglia (also referred to as the sympathetic chain, sympathetic trunk or the gangliated cord) running on each side of the spinal column, which communicate with the central nervous system via a branch to a corresponding spinal nerve. The sympathetic trunks extend from the base of the skull to the coccyx. The cephalic end of each is continued upward through the carotid canal into the skull, and forms a plexus on the internal carotid artery; the caudal ends of the trunks converge and end in a single ganglion, the ganglion impar, placed in front of the coccyx. As partly shown is FIG. 1, the ganglia of each trunk are distinguished as cervical, thoracic, lumbar, and sacral and, except is the neck, they closely correspond in number to the vertebrae.

The SNS controls a variety of autonomic functions including, but not limited to, control of movement and secretions from viscera and monitoring their physiological state, stimulation of the sympathetic system inducing, e.g., the contraction of gut sphincters, heart muscle and the muscle of artery walls, and the relaxation of gut smooth muscle and the circular muscles of the iris. The chief neurotransmitter in the SNS is adrenaline, which is liberated in the heart, visceral muscle, glands and internal vessels, with acetylcholine acting as a neurotransmitter at ganglionic synapses and at sympathetic terminals in skin and skeletal muscles. The actions of the SNS tend to be antagonistic to those of the PNS.

The neurotransmitter released by the post-ganglionic neurons is nonadrenaline (also called norepinephrine). The action of noradrenaline on a particular structure, such as a gland or muscle, is excitatory in some cases and inhibitory in others. At excitatory terminals, ATP may be released along with noradrenaline. Activation of the SNS may be characterized as general because a single pre-ganglionic neuron usually synapses with many post-ganglionic neurons, and the release of adrenaline from the adrenal medulla into the blood ensures that all the cells of the body will be exposed to sympathetic stimulation even if no post-ganglionic neurons reach them directly.

The present disclosure relates generally to neuromodulatory devices, systems and methods, and more particularly to devices, systems, and methods for treating PTSD in a subject. The ANS, and in particular the SNS, plays a crucial role in patients with PTSD. Part of the proposed pathophysiology of PTSD is that systemic autonomic responses to traumatic memories or contest produce full blown physiological responses (e.g., anxiety, racing heart, dry mouth, sweating, etc.) that feed hack to increase the level of emotional arousal and anxiety. As described in detail below, the present disclosure advantageously provides devices, systems, and methods for modulating the descending nerve signals from the brain through the SNS to peripheral tissues (e.g., cardiac, gastric, vascular, immunological, and other related tissues/organs), as well as ascending signals into the central nervous system to effectively normalize or regulate the SNS. By employing such devices, systems and methods, the present disclosure can treat PTSD by, for example, replacing conventional modalities, such as pharmacological blockade of the stellate ganglion.

Therapy Delivery Devices and Systems

In one aspect, the present disclosure includes various therapy delivery devices (not shown) and related systems configured to treat PTSD in a subject. In some instances, therapy delivery devices that may be used to practice the present disclosure may be positioned directly on or in target sympathetic nervous tissue, such as a ganglion of the SNS. In other instances, therapy delivery devices that may be used to practice the present disclosure can be positioned below the skin of a subject but not directly on or in target sympathetic nervous tissue. In further instances, therapy delivery devices that may be used to practice the present disclosure can comprise external devices, e.g., positioned in a lumen adjacent target sympathetic nervous tissue. In still further instances, therapy delivery devices used to practice the present disclosure can comprise an external device, e.g., positioned on the skin of a subject adjacent target sympathetic nervous tissue. Therapy delivery devices can be temporarily or permanently implanted within, on, or otherwise associated with a subject suffering from, afflicted by, or suspected of having PTSD.

Therapy delivery devices of the present disclosure cam be configured to deliver various types of therapy signals to target sympathetic nervous tissue, such as a ganglion of the SNS. For example, therapy delivery devices of the present disclosure can be configured to deliver only electrical energy, only magnetic, only a pharmacological or biological agent, or a combination thereof. In one example, therapy delivery devices of the present disclosure can comprise at least one electrode and an integral or remote power source, which is in electrical communication with the one or more electrodes and configured to produce one or more electrical signals (or pulses). In another example, therapy delivery devices can include a pharmacological or biological agent reservoir, a pump, and a fluid dispensing mechanism. Non-limiting examples of pharmacological and biological agents can include chemical compounds, drugs (e.g., prazosin, clonidine), nucleic acids, polypeptides, stem cells, toxins (e.g., botulinum), as well as various energy forms, such as ultrasound, radiofrequency (continuous or poised), magnetic waves, cryotherapy, and the like. In yet another example, therapy delivery devices can be configured to deliver magnetic nerve stimulation with desired field focality and depth of penetration. One skilled in the art will appreciate that combinations of the therapy delivery devices above configurations are also included within the scope of the present disclosure.

Figure 2:
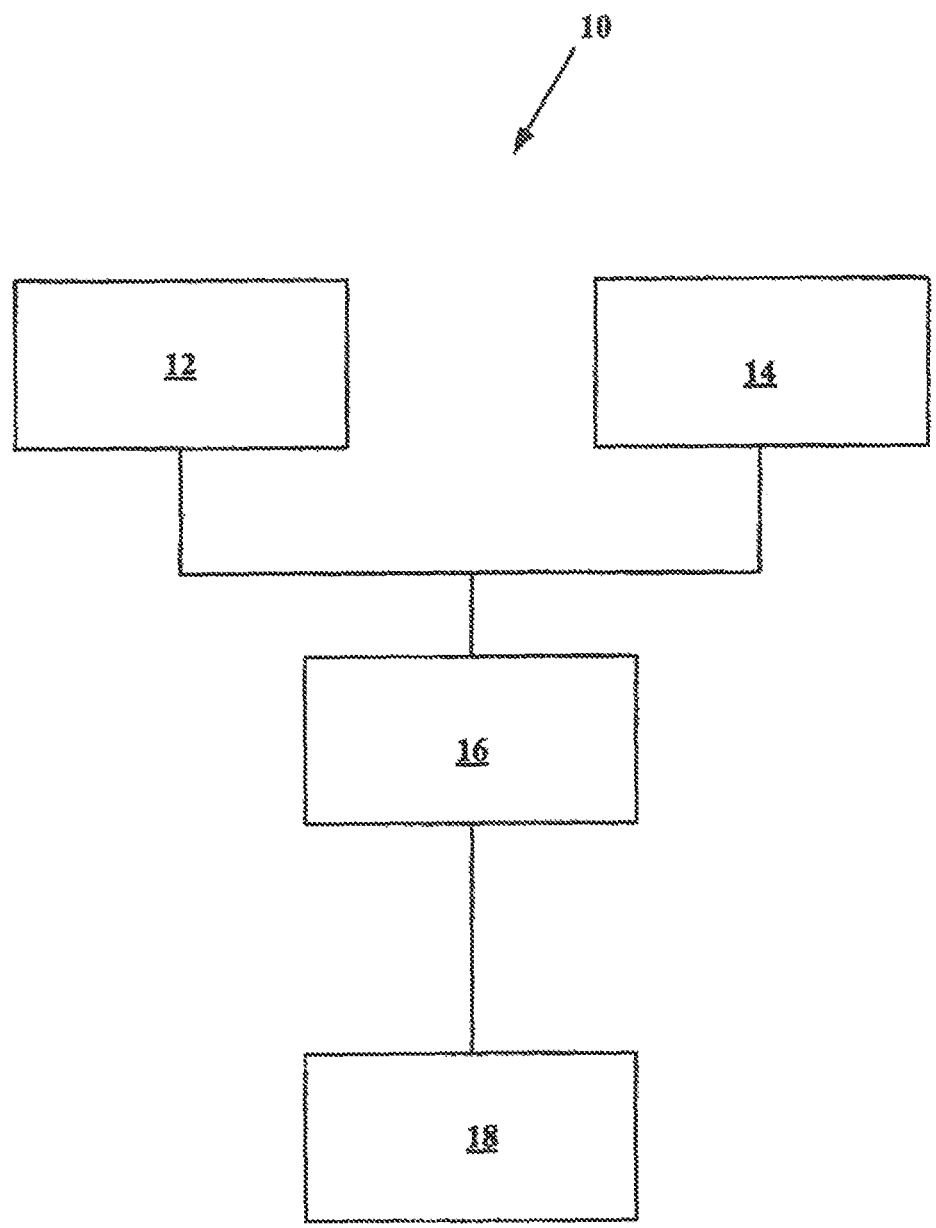
FIG. 2 is a schematic illustration showing a closed-loop therapy delivery system for treating post-traumatic stress disorder (PTSD) configured according to one aspect of the present disclosure.

In some instances, therapy delivery devices can comprise a stimulator (or inhibitor), such as an electrode, a controller or programmer, and one or more connectors (e.g., leads) for connecting the stimulating (or inhibiting) device to the controller. In one example, which is described in former detail below, the present disclosure can include a closed-loop therapy delivery system 10 (FIG. 2) for treating PTSD. As shown in FIG. 2, the therapy delivery system 10 can include a sensing component 12, a delivery component 14, a controller 16, and a power source 18. Each of the sensing component 12, delivery component 14, controller 16, and power source 18 can be in electrical communication with one another (e.g., via a physical connection, such as a lead, or a wireless link). In some instances, each of the sensing and delivery components 12 and 14 can comprise an electrode. In other instances, the delivery component 14 can comprise a coil configured to deliver magnetic stimulation. In further describing representative electrodes, which are described in the singular, it will be apparent that more than one electrode may be used as part of a therapy delivery device. Accordingly, the description of a representative electrode suitable for use in the therapy delivery devices of the present disclosure is applicable to other electrodes that may be employed.

An electrode can be controllable to provide output signals that may be varied in voltage, frequency, pulse-width, current and intensity. The electrode can also provide both positive and negative current flow from the electrode and/or is capable of stopping current flow from the electrode and/or changing the direction of current flow from the electrode. In some instances, therapy delivery devices can include an electrode that is controllable, i.e., in regards to producing positive and negative current flow from the electrode, stopping current flow from the electrode, changing direction of current flow from the electrode, and the like. In other instances, the electrode has the capacity for variable output, linear output and short pulse-width, as well as paired pulses and various waveforms (e.g., sine wave, square wave, and the like).

The power source 18 can comprise a battery or generator, such as a pulse generator that is operatively connected to an electrode via the controller 16. The power source 18 can be configured to generate an electrical signal or signals. In one example, the power source 18 can include a battery that is rechargeable by inductive coupling. The power source 18 may be positioned in any suitable location, such as adjacent the electrode (e.g., implanted adjacent the electrode), or a remote site in or on the subject's body or away from the subject's body in a remote location. An electrode may be connected to the remotely positioned power source 18 using wires, e.g., which may be implanted at a site remote from the electrode(s) or positioned outside the subject's body. In one example, an implantable power source 18 analogous to a cardiac pacemaker may be used.

The controller 16 can be configured to control the pulse waveform, the signal pulse width, the signal pulse frequency, the signal poise phase, the signal pulse polarity, the signal pulse amplitude, the signal pulse intensity, the signal pulse duration, and combinations thereof of an electrical signal. In other instances, the controller 16 can be configured to control delivery of magnetic energy or stimulation to the delivery component 14. The controller 16 may be used to convey a variety of currents and voltages to one or more electrodes and thereby modulate the activity of a target sympathetic nervous tissue. The controller 16 may be used to control numerous electrodes independently or in various combinations as needed to provide stimulation or inhibition of nerve activity. In some instances, an electrode may be employed that includes its own power source, e.g., which is capable of obtaining sufficient power for operation from surrounding tissues in the subject's body, or which may be powered by bringing a power source 18 external to the subject's body into contact with the subject's skin, or which may include an integral power source.

The electrical signal (or signals) delivered by the controller 16 to the delivery component 14 may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA and even more specifically from about 0.1 mA to about 25 mA. Similarly, the voltage may range from about 0.1 millivolt to about 25 volts, or about 0.5 to about 4000 Hz, with a pulse-width of about 5 microseconds to about 5000 Hz and more specifically from about 10 to about 1000 microseconds. In one example, the electrical signal can be oscillatory. The frequency may range from about 5 Hz to about 25,000 Hz. The type of stimulation may vary and involve different waveforms known to the skilled artisan. For example, the stimulation may be based on the H waveform found in nerve signals (i.e., Hoffinan Reflex). In another example, different forms of interferential stimulation may be used.

To increase nerve activity in a portion of the SNS, for example, voltage or intensity may range from about 1 millivolt to about 1 volt or more, e.g., 0.1 to about 50 mA or volts (e.g., from about 0.2 volts to about 20 volts), and the frequency may range from about 1 Hz to about 2500 Hz, e.g., about 1 Hz to about 10,000 Hz (e.g., from about 2 Hz to about 100 Hz). In some instances, pure DC and/or AC voltages may be employed. The pulse-width may range from about 1 microsecond to about 10,000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g., about several seconds). In some instances, stimulation may be applied for as long as about 1 minute or more, e.g., about several minutes or more (e.g., about 30 minutes or more).

To decrease activity in a portion of the ANS, for example, voltage or intensity may range from about 1 millivolt to about 1 volt or more. e.g., 0.1 to about 50 mA or volts (e.g., from about 0.2 volts to about 20 volts), and the frequency may range from about 1 Hz to about 10,000 Hz, e.g., about 50 Hz to about 2500 Hz. In one example, an electrical signal can have a frequency range of about 10,000 Hz or greater (e.g., high frequency stimulation) to effectively block nerve conduction. In certain embodiments, the frequency ranges from about 10,000 Hz to about 25,000 Hz. In some instances, pure DC and/or AC voltages may be employed. The pulse-width may range from about 1 microseconds to about 10,000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g., about several seconds). In some instances, the electrical energy may be applied for as long as about 1 minute or more, e.g., about several minutes or more (e.g., about 30 minutes or more may be used).

In some instances, the controller 16 can be configured to deliver an electrical signal to the delivery component 14 so that activity of a sympathetic nervous tissue (e.g., a ganglion of the SNS) is continuously and substantially blocked. Prior art methods for delivering electrical signals to sympathetic nervous tissue (e.g., the stellate ganglion) include application of pulsed radiofrequency (PRF) to reduce sympathetic activity. PRF is characterized by delivery of high-intensity current in pulses; during each cycle, an active phase is followed by a silent phase. Although PRF increases the temperature of the target tissue, the silent phase allows heat to dissipate so that neurodestructive temperatures are not reached. PRF does not provide a continuous reduction or blockade of nerve activity, however, since current is not applied during the silent phase. Advantageously, one example of the present disclosure includes continuous application of an electrical signal that substantially blocks or reduces sympathetic nerve activity without an increase in temperature of the target sympathetic nervous tissue. As described in more detail below, application of such an electrical signal can be performed by the closed-loop system 10 of the present disclosure to effectively normalize or regulate intrinsic sympathetic activity or tone in a subject diagnosed with, or suspected of having PTSD.

The electrode may be mono-polar, bipolar or multi-polar. To minimize the risk of an immune response triggered by the subject against the therapy delivery device, and also to minimize damage thereto (e.g., corrosion from other biological fluids, etc.), the electrode (and any wires and optional housing materials) can be made of inert materials, such as silicon, metal, plastic and the like. In one example, a therapy delivery device can include a multi-polar electrode having about four exposed contacts (e.g., cylindrical contacts).

As discussed above, the controller 16 (or a programmer) may be associated with a therapy delivery device. The controller 16 can include, for example, one or more microprocessors under the control of a suitable software program. Other components of a controller 16, such as an analog-to-digital converter, etc., will be apparent to those of skill in the art. In some instances, the controller 16 can be configured to record and store data indicative of the intrinsic sympathetic tone or activity in the subject. Therefore, the controller 16 can be configured to apply one or more electrical signals to the delivery component 14 when the intrinsic sympathetic tone or activity of a subject increases or decreases above a certain threshold value (or range of values).

Therapy delivery devices can be pre-programmed with desired stimulation parameters. Stimulation parameters can be controllable so that an electrical signal may be remotely modulated to desired settings without removal of the electrode from its target position. Remote control may be performed, e.g., using conventional telemetry with an implanted power source 18, an implanted radiofrequency receiver coupled to an external transmitter, and the like. In some instances, some or all parameters of the electrode may be controllable by the subject, e.g., without supervision by a physician. In other instances, some or all parameters of the electrode may be automatically controllable by a controller 16.

In one example, the therapy delivery device can be configured for percutaneous placement or implantation. In this instance, the therapy delivery device can comprise one or more implantable electrodes shaped or configured, for example, as a wire, a rod, a filament, a ribbon, a cord, a tube, a formed wire, a flat strip, or a combination thereof. In one example, one or more of the electrodes can comprise a laminotomy electrode array. Laminotomy electrodes, for example, generally have a flat paddle configuration and typically possess a plurality of electrodes (e.g., 2, 3, 4 or more) arranged on the paddle. The arrangement of electrodes on the paddle may be in rows and columns, staggered, spaced, circular, or any other arrangement that will position the electrodes for optimal delivery of electrical energy. The one or more implantable electrodes may be controlled individually, in series, in parallel, or any other manner desired. Once implanted, the implantable electrode(s) may be held in position using any method known to the skilled artisan, such as stitches, epoxy, tape, glue, sutures, or a combination thereof.

In another example, the therapy delivery device can be configured for intra vascular or intraluminal placement or implantation. In some instances, a therapy delivery device configured for intravascular or intraluminal placement or implantation can be configured in an identical or similar manner as the expandable electrode disclosed in U.S. patent application Ser. No. 11/641,331 to Greenberg et al. (hereinafter, "the '331 application"). In one example, the therapy delivery device can be configured for intravascular or intraluminal placement or implantation at an implantation site that is adjacent, or directly adjacent, target sympathetic nervous tissue (e.g., a ganglion of the SNS).

In yet another example, the therapy delivery device can be configured for transcutaneous neuromodulation. In some instances, transcutaneous neuromodulation can include positioning an electrode (or electrodes) or a magnetic coil on a skin surface so that an electrical signal can be delivered to target sympathetic nervous tissue, such as a ganglion of the SNS. Transcutaneous neuromodulation can additionally include partially transcutaneous methods (e.g., using a fine, needle-like electrode to pierce the epidermis). In other instances, a surface electrode (or electrodes) can be placed into electrical contact with target sympathetic nervous tissue (e.g., a ganglion of the SNS) associated with PTSD. In one example, a transcutaneous neuromodulation device can be used to modulate stellate ganglion activity. Generally, an electrical signal used for transcutaneous neuromodulation may be constant, varying and/or modulated with respect to the current, voltage, pulse-width, cycle, frequency, amplitude, and so forth (e.g., the current may be between about 1 to 100 microampere), about 10 V (average), shout 1 to about 1000 Hz or more, with a pulse-width of about 250 to about 500 microseconds.

In another example, the present disclosure can include a therapy delivery device or system configured for transcutaneous neuromodulation using magnetic stimulation. A magnetic stimulation device or system can generally include a pulse generator (e.g., a high current pulse generator) and a stimulating coil capable of producing magnetic pulses with desired field strengths. Other components of a magnetic stimulation device can include transformers, capacitors, microprocessors, safety interlocks, electronic switches, and the like. In operation, the discharge current flowing through the stimulating coil can generate the desired magnetic field or lines of force. As the lines of force cut through tissue (e.g., neural tissue), a current is generated in that tissue. If the induced current is of sufficient amplitude and duration such that the cell membrane is depolarized, nervous tissue will be stimulated in the same manner as conventional electrical stimulation. It is therefore worth noting that a magnetic field is simply the means by which an electrical current is generated within the nervous tissue, and that it is the electrical current, and not the magnetic field, which causes the depolarization of the cell membrane and thus stimulation of the target nervous tissue. Thus, in some instances, advantages of magnetic over electrical stimulation can include: reduced or sometimes no pain; access to nervous tissue covered by poorly conductive structures; and stimulation of nervous tissues lying deeper in the body without requiring invasive techniques or very high energy pulses.

Non-limiting examples of transcutaneous neuromodulation devices that may be used for treating PTSD are disclosed in U.S. Provisional Patent Application Ser. Nos. 61/693,946, filed Sep. 19, 2012, and 61/702,876, filed Aug. 28, 2012. It will be appreciated that transcutaneous therapy delivery devices and systems can additionally or optionally include any wearable item, accessory, article of clothing, or any object, device, or apparatus that a subject can use and, during use, comes into close or direct contact with a portion of the subject's body (e.g., the subject's neck). Examples of such transcutaneous neuromodulation devices can include vests, sleeves, shirts, socks, shoes, underwear, belts, scarves, wrist bands, gloves, ear pieces, band-aids, turtle neck, pendants, buttons, earrings, stickers, patches, bio-films, skin tattoos (e.g., using neuro-paint), chairs, computers, beds, head rests (e.g., of a chair or car seat), cell phones, and the like.

Therapy delivery devices can be part of an open- or closed-loop system. In an open-loop system, for example, a physician or subject may, at any time, manually or by the use of pumps, motorized elements, etc., adjust treatment parameters, such as pulse amplitude, pulse-width, pulse frequency, duty cycle, dosage amount, type of pharmacological or biological agent, etc. Alternatively, in a closed-loop system 10 (as discussed above), treatment or stimulation parameters, as described herein, of the electrical signals may be automatically adjusted in response to a sensed physiological parameter or a related symptom or sign indicative of the extent and/or presence of PTSD. In a closed-loop feedback system 10, a sensing component 12 can comprise a sensor (not shown in detail) that senses a physiological parameter associated with PTSD can be utilized. More detailed descriptions of sensors that may be employed in closed-loop systems, as well as other examples of sensors and feedback control techniques that may be employed as part of the present disclosure are disclosed in U.S. Pat. No. 5,716,377. One or more sensing components 12 can be implanted on or in any tissue or organ of a subject. For example, a sensing component 12 can be implanted in or on a component of the ANS, such as nerves, ganglia, afferents or efferents, or the spinal cord. Alternatively or additionally, a sensing component 12 can be implanted on or in a body organ and/or an anatomical connection thereof.

It should be appreciated that implementing a therapy delivery device as part of a closed-loop system can include placing or implanting a therapy delivery device on or within a subject at a target sympathetic nerve tissue (e.g., a ganglion of the SNS), sensing a physiological parameter associated with PTSD, and then activating the therapy delivery device to apply an electrical signal (or magnetic field) to adjust stimulation or treatment parameters, as described herein, of the electrical signal to the target sympathetic nerve tissue in response to the sensor signal. In some instances, such physiological parameters can include any characteristic, sign, symptom, or function associated with PTSD, such as a chemical moiety or nerve activity (e.g., electrical activity). Examples of such chemical moieties and nerve activities can include the activity of a sympathetic ganglia (or ganglion), protein concentrations, electrochemical gradients, hormones (e.g., cortisol), neuroendocrine markers, such as corticosterone, norepinephrine and melatonin, electrolytes, laboratory values, vital signs (e.g., blood pressure), markers of locomotor activity, cardiac markers (e.g., EKG RR intervals), abnormal levels of nerve growth factor, or other signs and biomarkers associated with PTSD.

Methods

Another aspect of the present disclosure includes methods for treating PTSD in subjects. In general, methods of the present disclosure can include the steps of: providing a therapy delivery device; placing the therapy delivery device into electrical communication with a target sympathetic nervous tissue (e.g., a ganglion of the SNS) associated wish PTSD: and activating the therapy delivery device to deliver an electrical signal (or magnetic field) to the target sympathetic nervous tissue so that activity of the target sympathetic nervous tissue is substantially blocked without enhancing a sign and/or symptom of PTSD. Subjects treatable by the present disclosure can, in some instances, be diagnosed with (or suspected of having) PTSD as well as one or more related or unrelated medical conditions. Non-limiting examples of medical conditions that can be co-treated by the methods of the present disclosure can include substance abuse, sleep deprivation or sleep disorders, psychiatric disturbances or diseases, and cardiac conditions.

In some instances, the step of placing a therapy delivery device into electrical communication with target sympathetic nervous tissue can entail different surgical and/or medical techniques, depending upon the target, for example. In some instances, a therapy delivery device can be surgically placed into electrical communication with target sympathetic nervous tissue via a percutaneous or endoscopic route. In other instances, a therapy delivery device can be placed into electrical communication with target sympathetic nervous tissue via an intravascular or intraluminal route. In further instances, a therapy delivery device can be placed into electrical communication with target sympathetic nervous tissue via a transcutaneous approach.

Examples of target sympathetic nervous tissue into which a therapy delivery device may be placed in electrical communication with can include, but are not limited to, a sympathetic chain ganglion, an efferent of a sympathetic chain ganglion, or an afferent of a sympathetic chain ganglion. In some instances, the sympathetic chain ganglion can be a cervical sympathetic ganglion, a thoracic sympathetic ganglion, or a stellate ganglion. Examples of cervical sympathetic ganglia can include an upper cervical sympathetic ganglion, a middle cervical sympathetic ganglion, or a lower cervical sympathetic ganglion. Examples of thoracic sympathetic ganglia can include a T1 sympathetic ganglia, a T2 sympathetic ganglia, a T3 sympathetic ganglia, a T4 sympathetic ganglia, a T6 sympathetic ganglia, or a T7 sympathetic ganglia.

After placing the therapy delivery device, the therapy delivery device can be activated to deliver an electrical signal (or magnetic field) to the target sympathetic nervous tissue and thereby substantially block the activity of the sympathetic nervous tissue without enhancing a sign and/or symptom of PTSD. The phrase "without enhancing" can mean that a particular symptom associated with PTSD is not increased. Therefore, in some instances, delivery of an electrical signal (or magnetic field) to the target sympathetic nervous tissue can prevent a sign and/or symptom associated with PTSD from either increasing or decreasing (as compared to a control or baseline). In other instances, delivery of an electrical signal (or magnetic field) to the target sympathetic nervous tissue can cause a sign and/or symptom associated with PTSD to decrease (as compared to a control or baseline). The therapy delivery device can be activated at the onset of an episode (e.g., the onset of a sign and/or symptom) associated with PTSD or, alternatively, the therapy delivery device can be activated continuously or intermittently to reduce or eliminate the frequency of such episode(s).

Delivery of the electrical signal (or magnetic field) to the target sympathetic nervous tissue can affect central motor output, nerve conduction, neurotransmitter release, synaptic transmission, and/or receptor activation. For example, the SNS may be electrically modulated to alter, shift, or change sympathetic activity from a first state to a second state, where the second state is characterized by a decrease in sympathetic activity relative to the first state. As discussed above, delivery of an electrical signal (or magnetic field) to the target sympathetic nervous tissue can substantially block activity of the target sympathetic nervous tissue. In some instances, delivery of the electrical signal (or magnetic field) to the target sympathetic nervous tissue can achieve a complete nerve conduction block of the target sympathetic nervous tissue for a desired period of time. In other instances, delivery of the electrical signal (or magnetic field) to the target sympathetic nervous tissue can achieve a partial block of the target sympathetic nervous tissue for a period of time, but long enough to decrease sympathetic nerve activity. The degree to which sympathetic activity is decreased can be titrated by one skilled in the art depending, for example, upon the nature and severity of PTSD in the subject.

Figure 3:
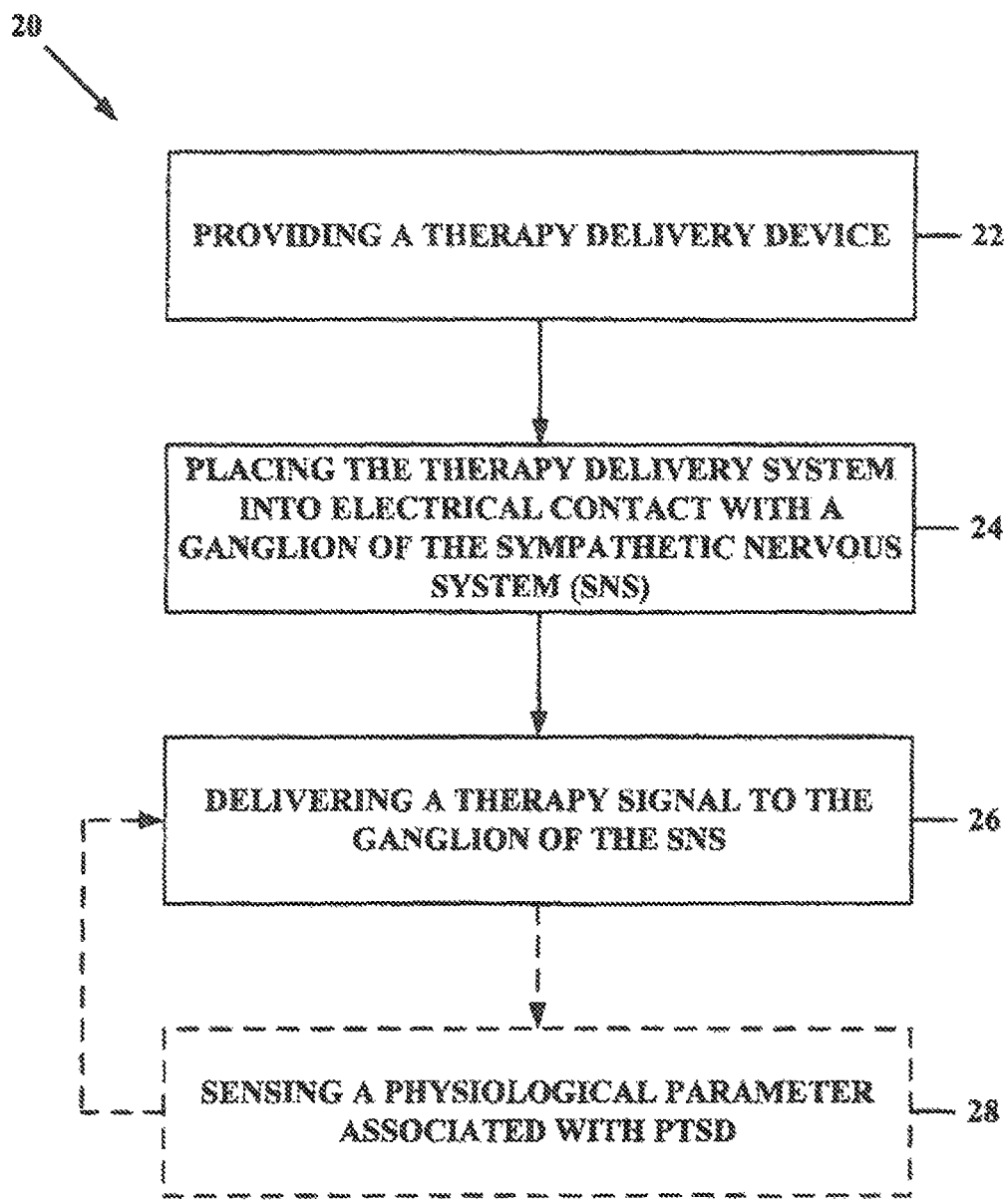
FIG. 3 is a process flow diagram illustrating a method for treating PTSD according to another aspect of the present disclosure.

In another aspect, the present disclosure can include a method 20 (FIG. 3) for treating PTSD in a subject. One step of the method 20 can include providing a therapy delivery device configured for placement and implantation within the subject (Step 22). In one example, the therapy delivery device can comprise an electrode array configured for percutaneous implantation in the subject. At Step 24, the therapy delivery device can be placed into direct electrical contact with target sympathetic nervous tissue, such as a ganglion of the SNS. In some instances, "direct electrical contact" can mean that the therapy delivery device is placed on or in the target sympathetic nervous tissue. In other instances, "direct electrical contact" can mean that the therapy delivery device is located adjacent or directly adjacent (but not in physical contact with) the target sympathetic nervous tissue such that delivery of an electrical signal can modulate a function, activity, and/or characteristic of the target sympathetic nervous tissue.

After placing the therapy delivery device into direct electrical contact with the target sympathetic nervous tissue, an electrical signal is delivered to the target sympathetic nervous tissue (Step 26). The therapy signal can be delivered in an amount and for a time sufficient to substantially block activity in the target sympathetic nervous tissue and thereby effect a decrease in sympathetic activity without enhancing a sign and/or symptom of PTSD. In one example, an electrical energy can be delivered to the stellate ganglion by an electrode or electrode array that is placed directly on or in the stellate ganglion. In some instances, PTSD may be caused by hypersympathetic activity, which may lead to increased adrenal gland function. In such instances, it may be desirable to deliver continuous blocking stimulation to the stellate ganglion to decrease sympathetic activity in the subject and thereby cause adrenal output to decrease (e.g., to a normal level).

Figure 4:
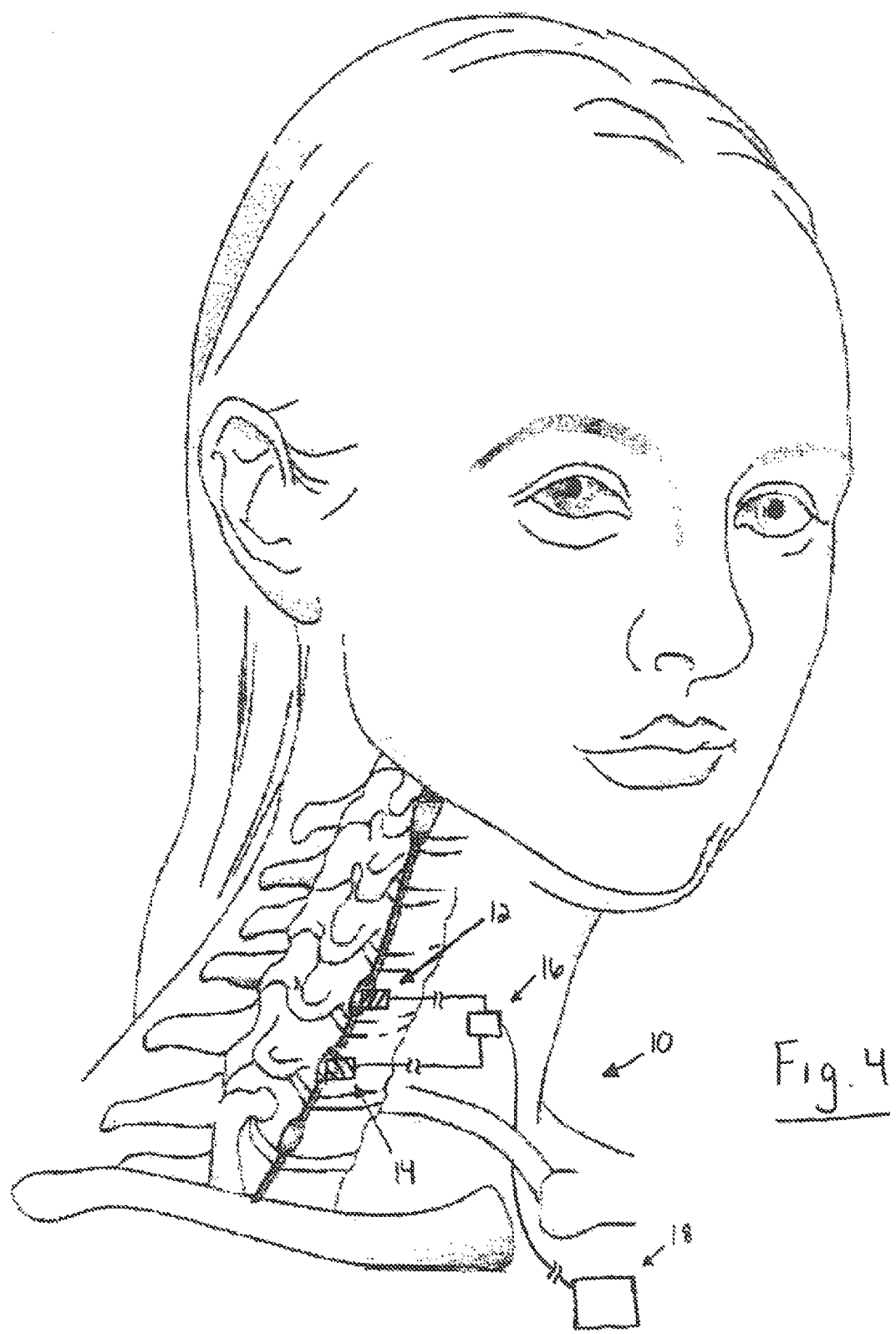
FIG. 4 is a schematic illustration showing the closed-loop therapy delivery system of FIG. 2 implanted is a subject.

One example of the method 20 is illustrated in FIG. 4. At Step 22, the method 20 can include providing a closed-loop therapy system 10 as described above. The closed-loop therapy system 10 can be configured for percutaneous implantation in the subject. As shown in FIG. 4, the system 10 can be implanted in the subject so that the delivery component 14 and the sensing component 12 are in direct electrical contact with the stellate ganglion and the middle cervical ganglion, respectively. Additionally, the system 10 can be implanted so that the controller 16 and the power source 18 are secured at the same or different subcutaneous locations.

Once the system 10 is implanted (Step 24), the sensing component 12 can detect electrical activity in the middle cervical ganglion, which may be indicative of intrinsic sympathetic tone in the subject. The detected level(s) of electrical activity can then be relayed to the controller 16, which determines if the detected level(s) is/are within a normal or abnormal range or level. Where the detected level(s) is/are within an abnormal range (e.g., at an elevated level as compared to a control or baseline), the controller 16 can cause the power source 18 to deliver an electrical signal to the delivery component 14. The electrical signal is then delivered to the stellate ganglion to substantially block activity therein (Step 26). While the electrical signal(s) is/are being delivered to the stellate ganglion, the sensing component 12 can continue to detect the level of electrical activity within the middle cervical ganglion (Step 28). When the level of electrical activity in the middle cervical ganglion is equal, or about equal to, a normal or baseline level, the controller 16 can cease delivery of the electrical signal(s) to the delivery component 14. Stimulation or treatment parameters, as described herein, can be adjusted during this process. By continuously or intermittently monitoring the intrinsic sympathetic tone or activity of the subject, the closed-loop therapy delivery system 10 can automatically decrease or normalize hypersympathetic activity and thus effectively treat PTSD.

Another aspect of the present disclosure can include transvascular or transluminal delivery of an electrical energy to a target sympathetic nervous tissue associated with PTSD. Thus, in some instances, the method 20 can include providing a therapy delivery device configured for transvascular or transluminal insertion and placement within the subject. For instance, a therapy delivery device configured for intravascular or intraluminal placement in a subject can include an expandable electrode as disclosed in the '331 application. The therapy delivery device can be inserted into a vessel or lumen of the subject. Non-limiting examples of vessel and lumens into which the therapy delivery device can be inserted include arteries, veins, an esophagus, a trachea, a vagina, a rectum, or any other bodily orifice. The therapy delivery device can be surgically inserted into the vessel or lumen via a percutaneous, transvascular, laparoscopic, or open surgical procedure.

After inserting the therapy delivery device bio the vessel or lumen, the therapy delivery device can be advanced (if needed) to an intraluminal target site so that the therapy delivery device is in electrical communication with, target sympathetic nervous tissue (e.g., a ganglion of the SNS). In some instances, advancement of the therapy delivery device can be done under image guidance (e.g., fluoroscopy, CT, MRI, etc.). Intraluminal target sites can include intravascular or intraluminal locations at which the therapy delivery device can be positioned. For example, an intraluminal target site can include a portion of a vessel wall that is innervated by (or in electrical communication with) the target sympathetic nervous tissue. Examples of intraluminal target sites can include, without limitation, vascular or luminal sites innervated by and/or in electrical communication with neurons, axons, fibers, tracts, nerves, plexus, afferent plexus fibers, efferent plexus fibers, ganglion, pre-ganglionic fibers, post-ganglionic fibers, cervical sympathetic ganglia/ganglion, thoracic sympathetic ganglia/ganglion, afferents thereof, efferents thereof, a sympathetic chain ganglion, a thoracic sympathetic chain ganglion, an upper cervical chain ganglion, a lower cervical ganglion, an inferior cervical ganglion, and a stellate ganglion.

After placing the therapy delivery device, an electrical signal is delivered to the target sympathetic nervous tissue. The therapy signal can be delivered in an amount and for a time sufficient to substantially block activity in the target sympathetic nervous tissue and thereby effect a decrease in sympathetic activity without enhancing a sign and/or symptom of PTSD.

In another aspect, the method 20 can include providing a therapy delivery device configured for placement on the skin of the mammal. Examples of therapy delivery devices configured for transcutaneous delivery of one or more therapy signals are disclosed above. In some instances, the therapy delivery device can be positioned about the subject, without penetrating the skin of the subject, so that the therapy delivery device is in electrical communication with target sympathetic nervous tissue (e.g., a ganglion of the SNS) associated with PTSD. Non-limiting examples of target sympathetic nervous tissue into which the therapy delivery device can be placed into electrical communication with can include neurons, axons, fibers, tracts, nerves, plexus, afferent plexus fibers, efferent plexus fibers, ganglion, pre-ganglionic fibers, post-ganglionic fibers, cervical sympathetic ganglia/ganglion, thoracic sympathetic ganglia/ganglion (e.g., a T2-T7 ganglion), afferents thereof, efferents thereof, a sympathetic chain ganglion, a thoracic sympathetic chain ganglion, an upper cervical chain ganglion, a lower cervical ganglion, an inferior cervical ganglion, and a stellate ganglion.

After placing the therapy delivery device, an electrical signal is delivered to the target sympathetic nervous tissue. The therapy signal can be delivered in an amount and for a time sufficient to substantially block activity in the target sympathetic nervous tissue and thereby effect a decrease in sympathetic activity without enhancing a sign and/or symptom of PTSD.

From the above description of the present disclosure, those skilled in the art will perceive improvements, changes and modifications. For example, while the present disclosure is discussed in terms of devices, systems, and methods for treating PTSD, it will be understood that the present disclosure may also be used to treat other anxiety disorders and disorders with psychotic features. Such improvements, changes, and modifications are within the skill of those in the art and are intended to be covered by the appended claims. All patents, patent applications, and publication cited herein are incorporated by reference in their entirety.

The following is claimed:

1. A closed-loop therapy delivery system for treating post-traumatic stress disorder (PTSD) in a subject, the therapy delivery system comprising:
    a sensing component configured to detect at least one physiological parameter associated with PTSD;
    a delivery component configured for implantation on or about a stellate ganglion of the sympathetic nervous system (SNS) to be in electrical communication with the stellate ganglion; and
    a controller configured to automatically coordinate operation of the sensing and delivery components;
    wherein the controller is programmed to deliver an electrical signal to the delivery component so that activity of the stellate ganglion of the SNS is continuously blocked to treat the PTSD without enhancing a symptom of PTSD.

2. The system of claim 1, wherein the electrical signal has a frequency range of about 10,000 Hz to about 25,000 Hz.

3. The system of claim 1, wherein all or only a portion of the system is implanted within the subject.

4. The system of claim 1, wherein the at least one physiological parameter includes a chemical moiety or an electrical activity.

5. The system of claim 1, wherein the controller is programmed to deliver an electrical signal to the delivery component without increasing the temperature of the stellate ganglion of the SNS.

6. The system of claim 1, wherein the controller is programmed to deliver magnetic energy to the stellate ganglion of the SNS.

7. A method for treating PTSD in a subject, the method comprising the steps of:
    placing a therapy delivery device into electrical communication with a stellate ganglion of the SNS; and
    activating the therapy delivery device to deliver an electrical signal to the stellate ganglion of the SNS so that activity of the stellate ganglion of the SNS is continuously blocked to treat the PTSD without enhancing a symptom of PTSD.

8. The method of claim 7, further comprising the steps of:
sensing at least one physiological parameter associated with PTSD;
    generating a sensor signal based on the at least one physiological parameter; and activating the therapy delivery device to adjust application of the electrical signal to the stellate ganglion of the SNS in response to the sensor signal to treat PTSD.

9. The method of claim 8, wherein the at least one physiological parameter includes a chemical moiety or an electrical activity.

10. The method of claim 7, wherein the electrical signal has a frequency range of about 10,000 Hz to about 25,000 Hz.

11. The method of claim 7, wherein the electrical signal is delivered to the stellate ganglion of the SNS without increasing the temperature of the stellate ganglion.

12. The method of claim 7, wherein the therapy delivery device is configured to deliver magnetic energy to the stellate ganglion of the SNS.

* * * * *